United States Patent [19]

Maesawa et al.

[11] Patent Number: 5,973,125
[45] Date of Patent: Oct. 26, 1999

[54] MACROAZO COMPOUND, A PROCESS FOR ITS PRODUCTION, A MACROAZO INITIATOR, AND A PROCESS FOR ITS USE

[75] Inventors: Tsuneaki Maesawa; Kazuo Shiraki; Nobutaka Shimamura, all of Kawagoe, Japan

[73] Assignee: Wako Pure Chemical Industries, Ltd., Osaka, Japan

[21] Appl. No.: 09/106,751

[22] Filed: Jun. 30, 1998

Related U.S. Application Data

[62] Division of application No. 08/888,625, Jul. 7, 1997, Pat. No. 5,854,406.

[30] Foreign Application Priority Data

Jul. 11, 1996 [JP] Japan .................................. 8-201278
Jul. 11, 1996 [JP] Japan .................................. 8-201279

[51] Int. Cl.$^6$ .................. C07C 245/00; C09B 29/00; C08K 5/23
[52] U.S. Cl. .................. 534/573; 524/190; 534/805; 534/806; 534/838; 534/851; 534/886
[58] Field of Search .............................. 534/886; 524/190

[56] References Cited

U.S. PATENT DOCUMENTS

| | | | |
|---|---|---|---|
| 2,586,995 | 2/1952 | Robertson | 534/838 |
| 2,666,758 | 1/1954 | Johnson | 534/838 |
| 3,306,888 | 2/1967 | Mortimer | 534/838 X |
| 3,649,614 | 3/1972 | Sheppard et al. | 534/886 X |
| 3,763,129 | 10/1973 | Sheppard et al. | 534/886 X |
| 3,868,359 | 2/1975 | Sheppard et al. | 534/886 X |
| 3,890,294 | 6/1975 | Sheppard et al. | 534/886 X |
| 3,956,269 | 5/1976 | Sheppard et al. | 534/886 X |
| 4,045,426 | 8/1977 | Sheppard et al. | 534/886 X |
| 4,075,286 | 2/1978 | Sheppard et al. | 534/886 X |
| 4,101,522 | 7/1978 | Sheppard et al. | 534/886 X |
| 4,218,370 | 8/1980 | Sheppard et al. | 534/886 X |
| 4,290,945 | 9/1981 | Syrov et al. | 534/886 X |
| 5,001,228 | 3/1991 | Shiraki et al. | 534/751 |

FOREIGN PATENT DOCUMENTS

| | | |
|---|---|---|
| 0 356 026 | 2/1990 | European Pat. Off. |
| 42 07 558 | 9/1993 | Germany |
| 64-62318 | 3/1989 | Japan |
| 1-247401 | 10/1989 | Japan |

OTHER PUBLICATIONS

*Chemical Abstracts*, vol. 88, No. 5, Jan. 30, 1998, p. 457, abstract No. 37278Q, Columbus, Ohio, US; F.R. Gritsenko et al.: "Azobisisobutyric acid beta–aminoethylamide".

Capek, Ignac et al. "On the kinetics of polymerization and copolymerization of poly(oxyethylene)macromonomers and styrene." *Makromol. Chem.*, 193, pp. 2843–2860, 1992.

*Kobunshi Ronbunshu*, vol. 44, No. 6, pp. 469–476, 1987.

*Primary Examiner*—Floyd D. Higel
*Attorney, Agent, or Firm*—Oliff & Berridge, PLC

[57] ABSTRACT

An azoamide compound of the formula:

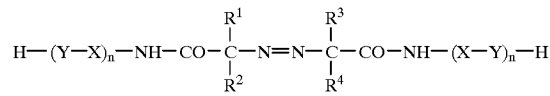

wherein $R^1$ through $R^4$ are independently an alkyl group; X is an alkylene groupl Y is —O— or —NH—; and n is an integer of 2 or more, is effective for producing a macroazo compound, which is a useful initiator for producing block copolymers.

18 Claims, No Drawings

MACROAZO COMPOUND, A PROCESS FOR ITS PRODUCTION, A MACROAZO INITIATOR, AND A PROCESS FOR ITS USE

This is a Divisional Application of application Ser. No. 08/888,625, filed Jul. 7, 1997, which issued as U.S. Pat. No. 5,854,406 on Dec. 29, 1998. The entire disclosure of the prior application is hereby incorporated by reference herein in its entirety.

BACKGROUND OF TEE INVENTION

The present invention relates to an azoamide compound excellent in the solubility in various solvents and useful as a polymerization initiator and the like; and to a novel macroazo compound having in one molecule two types of azo groups different from each other in the decomposition activity.

In the recent years, polymeric compounds have progressed from general purpose polymer to functional polymer, and block polymers which can be expected to manifest various functions effectively are being watched with interest. In such a state of things, an attempt to prepare a block polymer by the use of an azo compound was proposed, and a straight chain high-polymeric azo compound having a plurality of azo groups on the main chain obtained through an alternating polycondensation of an azo compound and a bifunctional compound was reported in JP-A-64-62318. However, the polymeric azo compounds reported in the above-mentioned patent gazette were made of a single azo compound, and therefore the azo groups existing on the main chain are all identical with each other in the decomposition activity. Thus, in order to leave a desired portion of the azo groups undecomposed in the first step of polymerization and to use the undecomposed portion of azo group in the second step of polymerization, it was necessary to control the temperature and time of polymerization strictly in the first step of polymerization. Further, the starting azo compound was inferior in solubility, so that no sufficient function as a polymerization initiator could be exhibited.

With the aim of solving these problems, an azo compound obtained by subjecting two kinds of azo compounds different in decomposition activity to a condensation reaction was reported (U.S. Pat. Nos. 3,763,129, No. 3,868,359, No. 3,649,614, No. 3,956,269, etc.). Such azo compounds, however, had at most 2 or 3 azo groups in one molecule, and therefore when such an azo compound was used as a polymerization initiator, the following difficulties arose: (1) a polymer of high molecular weight was difficult to obtain, (2) when the number of azo groups was 2, only an AB type polymer could be obtained, while when the number of azo group was 3, only an ABA type polymer could be obtained (A is a segment derived from a monomer A and B is a segment derived from a monomer B, hereinafter the same), (3) a number of radicals derived from the initiator, not participating in the polymerization, were formed, and (4) the kind of monomer which can be polymerized by this method was limited, because the azo compound was low in solubility in itself.

SUMMARY OF THE INVENTION

In view of the above, it is an object of the present invention to provide a novel azo compound excellent in solubility in various solvents, and to provide a novel macroazo compound obtained from said azo compound and excellent in solubility in various solvents, said macroazo compound being usable as a macroazo initiator for producing a block polymer easily and in a high efficiency without needing any strict control.

The present invention provides an azoamide compound represented by the following formula:

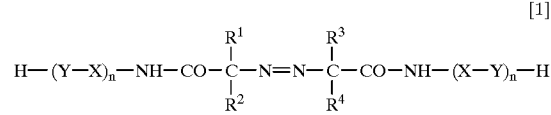

[1]

wherein $R^1$ to $R^4$ are independently an alkyl group; X is an alkylene group; Y is O or NH provided that a plurality of Y may be the same or different; and n is an integer of 2 or more.

The present invention also provides a process for producing the above-mentioned azoamide compound which comprises reacting an azodicarboxylic acid diester compound represented by the following formula:

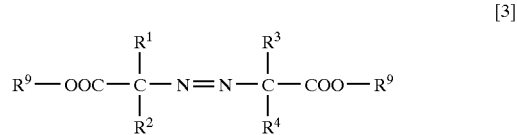

[3]

wherein $R^9$ is a lower alkyl group; and $R^1$ to $R^4$ are as defined above, with an aminoalcohol or a diamine represented by the following formula:

[4]

wherein X, Y and n are as defined above.

The present invention further provides a polymerization initiator comprising the above-mentioned azoamide compound, a polymerization process using said polymerization initiator, a macroazo compound obtained by said polymerization process, and a polymerization process of a monomer using said macroazo compound.

DESCRIPTION OF THE PREFERRED EMBODIMENTS

The present invention relates to an azoamide compound represented by the following formula:

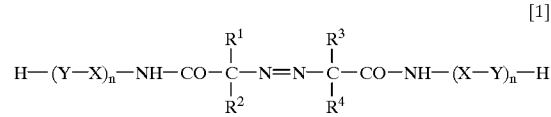

[1]

wherein $R^1$ to $R^4$ are independently an alkyl group; X is an alkylene group; Y is O or NH provided that a plurality of Y may be the same or different; and n is an integer of 2 or more.

The present invention further relates to a process for producing the above-mentioned azoamide compound which comprises reacting an azodicarboxylic acid diester compound represented by the following formula:

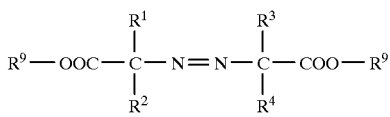

[3]

wherein $R^9$ is a lower alkyl group; and $R^1$ to $R^4$ are as defined above, with an aminoalcohol or a diamine represented by the following formula:

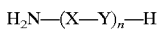

[4]

wherein X, Y and n are as defined above.

The present invention further relates to a polymerization initiator comprising the above-mentioned azoamide compound.

The present invention further relates to a process for polymerization which comprises using the above-mentioned azoamide compound as a polymerization initiator.

The present invention further relates to a macroazo compound constituted of repeating units represented by the following formula:

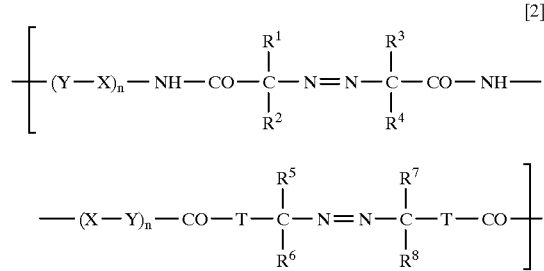

[2]

wherein $R^5$ and $R^7$ are independently an alkyl group; $R^6$ and $R^8$ are independently an alkyl group or a cyano group; T is an alkylene group; and $R^1$ to $R^4$, X, Y and n are as defined above; provided that the degree of polymerization of said macroazo compound is 2 or more.

The present invention further relates to a process for producing a macroazo compound which comprises reacting the above-mentioned azoamide compound with an azodicarboxylic acid compound represented by the following formula:

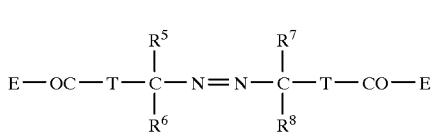

[7]

wherein $R^5$ and $R^7$ are independently an alkyl group; $R^6$ and $R^8$ are independently an alkyl group or a cyano group; T is an alkylene group; and E is a hydroxyl group or Z; and Z is a halogen atom.

The present invention further relates to a macroazo initiator comprising the above-mentioned macroazo compound.

The present invention further relates to a process for polymerization which comprises using the above-mentioned macroazo initiator.

The present invention further relates to a process for producing a block polymer which comprises using the above-mentioned macroazo initiator.

The alkyl group represented by $R^1$ to $R^4$ in the formulas [1], [2] and [3] and the alkyl group represented by $R^5$ to $R^8$ in the formulas [2] and [7] may be any of straight chain, branched chain and cyclic alkyl groups, of which examples are lower alkyl groups such as alkyl groups having 1–6 carbon atoms. Specific examples thereof include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, a 3,3-dimethylbutyl group, a 1,1-dimethylbutyl group, a 1-methylpentyl group, a n-hexyl group, an isohexyl group, a cyclopropyl group, a cyclopentyl group, a cyclohexyl group and the like.

The alkylene group represented by X in the formulas [1], [2] and [4] may be any of straight chain, branched chain and cyclic alkylene groups, of which examples are alkylene groups having 1–10 carbon atoms. Specific examples thereof include a methylene group, an ethylene group, a propylene group, a butylene group, a 2-methylpropylene group, a pentylene group, a 2,2-dimethylpropylene group, a 2-ethylpropylene group, a hexylene group, a heptylene group, an octylene group, a 2-ethylhexylene group, a nonylene group, a decylene group, a cyclopropylene group, a cyclopentylene group, a cyclohexylene group and the like. Of these alkylene groups, particularly preferred are alkylene groups having 1–6 carbon atoms. The groups represented by X which are present in the number of n may be identical with or different from one another. Y is O or NH, and a plurality of groups represented by Y, which is present in the number of n, may be identical with (only O or NH) or different from one another (O and NH being present). The number n is usually 2 or more and, preferably 2–50, and more preferably 2–30, further preferably 2–10, and most preferably 2–4.

The alkylene group represented by T in the formulas [2] and [7] may be any of straight chain, branched chain and cyclic alkylene groups, of which examples are alkylene groups having 1–10 carbon atoms. Specific examples thereof include a methylene group, an ethylene group, a propylene group, a butylene group, a 2-methylpropylene group, a pentylene group, a 2,2-dimethylpropylene group, a 2-ethylpropylene group, a hexylene group, a heptylene group, an octylene group, a 2-ethylhexylene group, a nonylene group, a decylene group, a cyclopropylene group, a cyclopentylene group, a cyclohexylene group and the like. Of these alkylene groups, particularly preferred are alkylene groups having 1–6 carbon atoms.

The lower alkyl group represented by $R^9$ in the formula [3] may be any of straight chain and branched chain alkyl groups, of which examples are alkyl groups having 1–6 carbon atoms. Specific examples thereof include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, a 3,3-dimethylbutyl group, a 1,1-dimethylbutyl group, a 1-methylpentyl group, a n-hexyl group, an isohexyl group and the like.

As the halogen atom represented by Z in the definition of E in the formula [7], fluorine, chlorine, bromine, iodine and the like can be referred to.

The azoamide compound represented by the above-mentioned formula [1] can be produced in the following manner.

That is, the azoamide compound can easily be obtained by reacting an azodicarboxylic acid diester compound represented by the following formula:

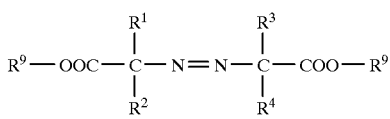

$$R^9-OOC-\underset{R^2}{\overset{R^1}{\underset{|}{\overset{|}{C}}}}-N=N-\underset{R^4}{\overset{R^3}{\underset{|}{\overset{|}{C}}}}-COO-R^9 \quad [3]$$

wherein $R^1$ to $R^4$ and $R^9$ are as defined above, with an aminoalcohol or a diamine represented by the following formula:

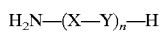

$$H_2N-(X-Y)_n-H \quad [4]$$

wherein X, Y and n are as defined above, in an appropriate solvent or in the absence of solvent, in the presence of an alkaline organic metal compound.

As the alkaline organic metal compounds which can be used in the production of the azoamide compound of the present invention, alkali metal alkoxides such as sodium methoxide, sodium ethoxide, potassium methoxide, potassium ethoxide, potassium tert-butoxide and the like; and organic lithium compounds such as n-butyllithium, tert-butyllithium and the like can be referred to.

The alkaline organic metal compound is used usually in an amount of 0.05–3 equivalents and preferably 0.1–0.5 equivalent per equivalent of azodicarboxylic acid diester compound, though the amount of the alkaline organic metal compound may vary depending on the kind of aminoalcohol or diamine.

The reaction solvents which can be used include hydrocarbons such as toluene, xylene, benzene, cyclohexane, n-hexane, n-octane and the like; alcohols such as methanol, ethanol, n-propanol, isopropanol, n-butanol, isobutanol, tert-butanol and the like; dimethylformamide, dimethyl sulfoxide, and the like. These solvents may be used singly or as a mixture thereof.

The amounts of the azodicarboxylic acid diester compound and the aminoalcohol (or diamine) used for production of the azoamide compound of the present invention vary depending on the kind of aminoalcohol (or diamine). However, the amount of the aminoalcohol (or diamine) is usually appropriately selected from a range of from 1.5 moles to 10 moles and preferably from a range of from 2 moles to 5 moles, per mole of the azodicarboxylic acid diester compound.

The reaction temperature is not particularly limited. If the reaction temperature is too high, however, decomposition of the azo group takes place. If the reaction temperature is too low, the reaction velocity is low and the production takes a long period of time. Accordingly, the reaction temperature is usually appropriately selected from a range of from 0° C. to 40° C.

The reaction time varies dependently on the kinds of the azodicarboxylic acid diester compound and the aminoalcohol (or diamine). Usually, however, the reaction time is appropriately selected from a range of from 1 hour to 24 hours.

As the azodicarboxylic acid diester compound and the aminoalcohol (or diamine) used in the present invention, commercial products may be used, and those produced appropriately according to the usual methods may also be used.

Since the azoamide compound thus obtained easily generates radical species with evolution of nitrogen gas by cleavage of azo groups upon heating or photo-irradiation, polymerization proceeds rapidly even if any of various monomers are present.

For polymerizing or copolymerizing a monomer by using the azoamide compound of the present invention as a polymerization initiator, the following procedure may be adopted, for example.

Thus, the azoamide compound of the present invention represented by the formula [1] and a monomer are subjected to a polymerization reaction according to the usual method in an appropriate solvent or in the absence of solvent, and optionally in the atmosphere of an inert gas.

After the reaction, a post-treatment and the like may be carried out according to the conventional procedures in this field of art.

If necessary, a chain transfer agent such as laurylmercaptan, octylmercaptan, butylmercaptan, 2-mercaptoethanol, butyl thioglycolate or the like may be added to the polymerization system in order to control the molecular weight.

As the monomer, vinyl monomers, diene monomers and the like can be referred to, for example.

Specific examples of the vinyl monomer include α-ethylenically aromatic hydrocarbons having 8–20 carbon atoms such as styrene, 4-methylstyrene, 4-ethylstyrene, 4-methoxystyrene, divinylbenzene and the like; vinyl esters having 3–20 carbon atoms such as vinyl formate, vinyl acetate, vinyl propionate, isopropenyl acetate and the like; halogen-containing vinyl compounds having 2–20 carbon atoms such as vinyl chloride, vinylidene chloride, vinylidene fluoride, tetrafluoroethylene, tetrachloroethylene and the like; ethylenic carboxylic acids having 3–20 carbon atoms such as acrylic acid, methacrylic acid, itanocnic acid, maleic acid, fumaric acid, crotonic acid, citraconic acid, methaconic acid, vinylacetic acid, allylacetic acid, vinylbenzoic acid and the like (these acids may be used in the form of a salt of alkali metal such as sodium, potassium and the like or ammonium salt, if necessary); ethylenic carboxylic esters having 4–20 carbon atoms such as methyl methacrylate, ethyl methacrylate, propyl methacrylate, butyl methacrylate, 2-ethylhexyl methacrylate, lauryl methacrylate, stearyl methacrylate, vinyl methacrylate, allyl methacrylate, phenyl methacrylate, benzyl methacrylate, methyl acrylate, ethyl acrylate, butyl acrylate, 2-ethylhexyl acrylate, lauryl acrylate, stearyl acrylate, vinyl acrylate, dimethyl itaconate, diethyl itaconate, dimethyl maleate, diethyl maleate, dimethyl fumarate, diethyl fumarte, methyl crotonate, ethyl crotonate, vinyl crotonate, dimethyl citraconate, diethyl citraconate, dimethyl methaconate, diethyl methaconate, methyl 3-butenoate, 2-hydroxyethyl methacrylate, 3-hydroxypropyl methacrylate, 2-hydroxypropyl methacrylate, 2-hydroxyethyl acrylate, 3-hydroxypropyl acrylate, 2-hydroxypropyl acrylate and the like; cyano-containing vinyl compounds having 3–20 carbon atoms such as acrylonitrile, methacrylonitrile, allyl cyanide and the like; vinyl amide compounds having 3–20 carbon atoms such as acrylamide, methacrylamide and the like; ethylenic aldehydes having 3–20 carbon atoms such as acrolein, crotonaldehyde and the like; vinylsulfonic acids having 2–20 carbon atoms such as vinylsulfonic acid, 4-vinylbenzene-sulfonic acid and the like (these acids may be used in the form of a salt of alkali metal salt such as sodium, potassium and the like, if necessary); vinyl aliphatic amines having 2–20 carbon atoms such as vinylamine, allylamine and the like; vinyl aromatic amines having 8–20 carbon atoms such as vinylaniline and the like; vinyl aliphatic heterocyclic amines having 5–20 carbon atoms such as N-vinylpyrrolidone, vinylpiperidine and the like; vinyl aromatic heterocyclic amines having 5–20 carbon atoms such as vinylpyridine, 1-vinylimidazole and the like; ethylenic alcohols having 3–20 carbon atoms such as allyl alcohol, crotyl alcohol and the like; and ethylenic phenols having 8–20 carbon atoms such as 4-vinylphenol and the like.

Specific examples of the diene monomer include diene compounds having 4–20 carbon atoms such as butadiene, isoprene and the like.

These monomers may be used either singly or in proper combination thereof.

As the method of the polymerization, solution polymerization, bulk polymerization, suspension polymerization, emulsion polymerization and the like can be referred to.

The solvents which can be used in the solution polymerization are, for example, ethers such as tetrahydrofuran, diethyl ether, dioxane and the like; halogenated hydrocarbons such as chloroform, methylene chloride, 1,2-dichloroethane, carbon tetrachloride, trichlorethylene and the like; hydrocarbons such as n-hexane, n-octane, cyclohexane, petroleum ether, toluene, benzene, xylene and the like; alcohols such as methanol, ethanol, n-propanol, isopropanol, n-butanol, isobutanol, tert-butanol and the like; ketones such as acetone, methyl ethyl ketone, methyl isobutyl ketone, cyclohexanone and the like; esters such as methyl acetate, ethyl acetate, n-butyl acetate, methyl propionate and the like; acetonitrile, N,N-dimethylformamide, N,N-dimethylacetamide, N-methylpyrrolidone, dimethyl sulfoxide, water and the like. These solvents may be used singly or as a mixture thereof.

The polymerization is preferably carried out in an atmosphere of inert gas. As the inert gas, nitrogen gas, argon gas and the like can be referred to.

In the practice of the polymerization reaction, the amount of the azoamide compound may vary depending on the kind of monomer used. Generally speaking, however, the amount of azoamide compound may be selected from a wide range. The amount of azoamide compound is usually from 0.01 to 100% by weight and preferably from 0.05 to 50% by weight, based on monomer.

Although concentration of the monomer at the time of polymerization may vary depending on the kind of monomer, it is appropriately selected usually from a range of 5 to 100% by weight and preferably from a range of 10 to 60% by weight.

The temperature of polymerization is not particularly limited. However, if the temperature of polymerization is too low, decomposition of the azo group cannot take place sufficiently, so that the polymerization progresses too slowly. If the temperature of polymerization is too high, decomposition of the azo group takes place too violently, so that the polymerization reaction is difficult to control. Accordingly, the temperature of polymerization is appropriately selected usually from a range of 20–150° C. and preferably from a range of 50–130° C.

Although the reaction time varies dependently on the kinds of azoamide compound and monomer and concentrations thereof, the reaction time is appropriately selected usually from a range of 2–24 hours.

The characteristic features of the azoamide compound of the present invention are as follows:

1) Since the azoamide compound of the present invention has reactive hydroxyl or amino group on the molecular terminal thereof, the azoamide compound is excellent in solubility in various solvents.

2) Into the molecular terminal of the polymer obtained by using the azoamide compound as a polymerization initiator, a hydroxyl or amino group derived from the azoamide compound can be introduced, and thereby various functions can be imparted to the polymer.

3) Since the polymer has reactive hydroxyl (or amino) group on the molecular terminal thereof, a reaction of the hydroxyl or amino group of such a polymer with a compound having reactive functional group can form a polymeric azo compound constituted of repeating units having many azo groups and excellent solubility.

4) Since the polymeric azo compound thus formed has an alkylene part in the molecule thereof through intermediation of O or NH, the polymeric azo compound is expected to be usable as an inclusion compound, if necessary.

The macroazo compound of the present invention constituted of the repeating unit represented by formula [2] can be produced from the azoamide compound of the present invention represented by formula [1], in the following manner.

Thus, one mole of the azoamide compound represented by formula [1] and 1–1.2 moles, preferably an equimolar quantity, of an azodicarboxylic acid compound represented by the following formula [5]:

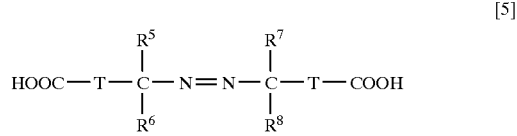

[5]

wherein $R^5$ to $R^8$ and T are as defined above, (a compound of the above-mentioned formula [7] wherein E is a hydroxyl group) are subjected to a polycondensation reaction by the use of a dehydrating agent in an appropriate solvent, if necessary in the presence of a basic catalyst, and if necessary in an atmosphere of an inert gas, by which the macroazo compound of the present invention can be formed.

Alternatively, the macroazo compound of the present invention constituted of the repeating unit of the formula [2] can easily be formed by the following method, too.

Thus, in the first step, an azodicarboxylic acid compound represented by the formula [5] is reacted with a halogenating agent in an appropriate solvent or in the absence of solvent at 0–120° C. for 0.5–20 hours. By this reaction, there can be obtained an azodicarboxylic acid dihalide represented by the following formula [6]:

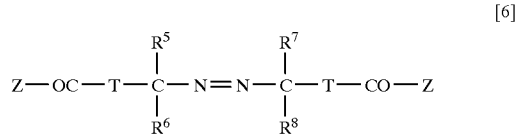

[6]

wherein $R^5$ to $R^8$, T and Z are as defined above (this compound is a compound of formula [7] wherein E is Z).

As said halogenating agent, thionyl chloride, thionyl bromide, phosphorus trichloride, phosphorus tribromide, phosphorus pentachloride, phosphorus oxychloride, phosphorus oxybromide and the like can be used.

The amount of the halogenating agent is appropriately selected usually from a range of 1.5 to 10 moles and preferably 2 to 5 moles, per mole of the azodicarboxylic acid compound.

In the subsequent step, one mole of the azoamide compound represented by the formula [1] and 1–1.2 moles, preferably an equimolar quantity, of the azodicarboxylic acid dihalide represented by the above-mentioned formula [6] are subjected to a polycondensation reaction in an appropriate solvent, if necessary in the presence of a basic catalyst, and if necessary in an atmosphere of an inert gas, by which the macroazo compound of the present invention can be obtained. The macroazo compound of the present invention thus obtained has a carbonyl halide group on one molecular terminal thereof (when the azoamide compound of the formula [1] is reacted with the azodicarboxylic acid compound represented by the formula [5], the product has a carboxyl group on one molecular terminal thereof). If necessary, the carbonyl halide group present on one molecular terminal can be converted to a carboxyl group by hydrolyzing the macroazo compound in the conventional manner.

In any of these two methods, the reaction solvents which can be used include ethers such as diethyl ether, diisopropyl ether, tetrahydrofuran, dioxane, dimethoxyethane and the like; halogenated hydrocarbons such as carbon tetrachloride, chloroform, methylene chloride, 1,2-dichloroethane, trichlorethylene and the like; hydrocarbons such as n-hexane, benzene, toluene, xylene and the like; esters such as ethyl acetate, butyl acetate, methyl propionate and the like; acetonitrile, N,N-dimethylformamide and the like. These solvents may be used either singly or as a mixture thereof.

The first method uses a dehydrating agent. The dehydrating agent is not particularly limited, so far as it is usable as a dehydrating condensing agent. Specific examples of said dehydrating agent include inorganic dehydrating agents such as concentrated sulfuric acid, diphosphorus pentoxide, anhydrous zinc chloride and the like; carbodiimides such as dicyclohexylcarbodiimide, diisopropylcarbodiimide, 1-ethyl-3-(3-dimethylaminopropylcarbodiimide) hydrochloride and the like; polyphosphoric acid, acetic anhydride, carbonyldiimidazole, p-toluenesulfonyl chloride and the like.

The amount of the dehydrating agent is not particularly limited. However, if the amount of the dehydrating agent is too small, the reaction progresses too slowly. The use of too large an amount of dehydrating agent, however, is uneconomical. Thus, the amount of the dehydrating agent is appropriately selected usually from a range of 1 to 5 moles and preferably from a range of 2 to 3 moles, per mole of the azoamide compound.

The polycondensation reaction is preferably carried out in the presence of a basic catalyst. Specific examples of said basic catalyst include organic amines such as triethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undec-7-ene, tri-n-butylamine, N-methylmorpholine and the like; metal hydrides such as sodium hydride and the like; and basic alkali metal compounds such as n-butyllithium, tert-butyllithium and the like.

The amount of the basic catalyst is appropriately selected usually from a range of 0.5–5 moles and preferably from a range of 1–2 moles, per mole of the azoamide compound.

If necessary, the polycondensation reaction may be carried out in an atmosphere of an inert gas. As the inert gas, nitrogen gas, argon gas and the like can be used.

The reaction temperature is not particularly limited. However, if the reaction temperature is too high, decomposition of the azo group is promoted. If the reaction temperature is too low, the velocity of reaction is low and the production takes too long a period of time. Thus, the reaction temperature is appropriately selected usually from a range of $-10°$ C. to $60°$ C. If necessary, the reaction temperature may be step-wise elevated from a low temperature. Although the reaction temperature varies depending on the method of production, it is appropriately selected usually from a range of 1–60 hours.

The objective product may be isolated from the reaction mixture by an appropriate method in accordance with the kinds and quantities of starting materials, basic catalyst, dehydrating agent and solvent, and the state of reaction mixture. For example, when the reaction mixture is a viscous liquid, the reaction mixture is diluted with an appropriate solvent and filtered to remove the impurities and thereafter the solvent is distilled off. In these manners, the objective macroazo compound is obtained.

As the azodicarboxylic acid compounds represented by the formula [5], any of commercially available products and those appropriately produced according to conventional methods may be used.

The macroazo compound of the present invention thus prepared is an oligomer of which degree of polymerization p is usually 2 or above, preferably 2–100, and further preferably about 2–30.

Since the macroazo compound of the present invention easily generates radical species with evolution of nitrogen gas by cleavage of azo groups upon heating or photo-irradiation, polymerization proceeds rapidly even if any of various monomers are present.

As is apparent from the above-mentioned formula [2], the macroazo compound of the present invention has two kinds of azo groups in the molecule thereof. The two kinds of azo groups are different from each other in the decomposing activity, because one of the two kinds of azo groups is linked to a carbon atom to which an alkylene group is linked through inter-mediation of an amide group, while the other kind of azo group is linked to a carbon atom to which an alkylene group is linked directly.

Accordingly, the macroazo compound of the A present invention is characterized in that it has two kinds of azo groups different from each other in decomposing activity in the molecule thereof. When the macroazo compound of the present invention is used as a macroazo initiator, it is possible to decompose the azo group of higher decomposing activity preferentially while hardly decomposing the azo group of lower decomposing activity by appropriately selecting the conditions of decomposition, by which there can be obtained a polymer in which the azo group of lower activity is left undecomposed. If a polymerization of the second step is carried out by the use of the remaining lower activity azo group, there can easily be obtained a block polymer block-wise containing different monomer constituents.

Production of the block polymer using the macroazo compound as a macroazo initiator can be practiced in the following manner, for example.

Thus, in the first step, the macroazo compound of the present invention represented by the formula [2] and a monomer are subjected to a polymerization reaction in the usual manner in an appropriate solvent or in the absence of solvent, if necessary in an atmosphere of inert gas, under such a condition as to preferentially decompose the azo group of higher activity while hardly decomposing the azo group of lower activity. Thus, an azo group-containing polymer can be obtained.

In the second step, the azo group-containing polymer and a monomer different from the monomer used in the first step are subjected to a polymerization reaction in the usual manner in an appropriate solvent or in the absence of solvent, if necessary in an atmosphere of an inert gas, by which the objective block polymer can be obtained.

After the reaction, a post-treatment and the like may be carried out according to the conventional procedures of after treatments in this field of art.

In carrying out the polymerization, a chain transfer agent such as laurylmercaptan, octylmercaptan, butylmercaptan, 2-mercaptoethanol, butyl thioglycolate or the like may be added if necessary, for the purpose of regulating the molecular weight.

As the method of polymerization, solution polymerization, bulk polymerization, suspension polymerization, emulsion polymerization and the like can be adopted.

As the monomers used in the first and second steps of the polymerization, all the monomers which can be used in -the polymerization or copolymerization using the azoamide compound of the present invention as a polymerization initiator can be used.

As the solvent used in the solution polymerization, all the solvents which have been mentioned above as solvents usable in the polymerization or copolymerization of monomer by the use of the azoamide compound of the present invention can be referred to.

The polymerization is preferably carried out in an atmosphere of inert gas. As the inert gas, nitrogen gas, argon gas and the like can be referred to.

Although the amount of the macroazo compound used in the polymerization may vary depending on the kind of monomer, it can be selected from a wide range. The amount of the macroazo compound is appropriately selected from a range of 0.01–100% by weight and preferably from a range of 0.05–50% by weight, based on the monomer(s).

Although concentration of monomer in the polymerization reaction may vary depending on the kind of monomer, it is appropriately selected usually from a range of 5–100% by weight and preferably from a range of 10–60% by weight.

Although the reaction temperature may be somewhat dependent on other polymerization conditions, it is usually selected from a range of 30° C. to 130° C. Preferably, the polymerization of the first step is carried out at a low temperature and the polymerization of the second step is carried out at a high temperature in order to obtain a block polymer effectively. The temperature of polymerization of the first step is preferably in the range of 50° C. to 80° C., and the temperature of polymerization of the second step is preferably in the range of 80° C. to 120° C.

Although the reaction time may vary depending on the reaction temperature, the kinds of azoamide compound and monomer to be reacted and the reaction conditions such as concentrations thereof, it is appropriately selected usually from a range of from 2 hours to 24 hours.

Generally speaking, high polymeric compounds cannot always be expressed by a simple structural formula because of complex structure. If the block polymer obtained in the above-mentioned manner is daringly expressed by a structural formula, it can be expressed by the following formula [8]:

[—{(M)$_a$}—{(N)$_b$}—]$_d$ [8]

because this polymerization reaction uses the macroazo compound constituted of a repeating unit of the above-mentioned formula [2] as a macroazo initiator, provided that M represents the unit derived from the monomer used in the polymerization of the first step, N represents the unit derived from the monomer used in the polymerization reaction of the second step, a and b each represents, independently of one another, a natural number, d represents an integer of at least 2, and {} embraces a random structure such as graft copolymer structure, block copolymer structure, etc.

In the above-mentioned manner, a block polymer can be produced easily and quite efficiently by using the macroazo compound of the present invention as a macroazo initiator.

The macroazo compound of the present invention can be used not only as a macroazo initiator for production of block polymer successfully as has been mentioned above, but also it can effectively be used as a radical polymerization initiator for polymerization of monomers, of course. In the radical polymerization using the macroazo compound of the present invention, the same monomers as used in the production of the block polymer can be used. As specific examples of said monomer, all the monomers previously mentioned as monomers usable for polymerization or copolymerization using the azo compound of the present invention as a polymerization initiator can be referred to. The method of polymerization is also the same as that of conventional polymerization using a radical polymerization initiator.

Since the macroazo compound of the present invention is characterized in that it can be used in the polymerization reactions using various solvents without trouble because of excellent solubility in various organic solvents.

Next, the present invention is explained in more detail with reference to the following Examples and Experimental Examples. The present invention is by no means limited by these Examples.

EXAMPLE 1

Synthesis of 2,2'-azobis[N-(2-hydroxyethoxy)-ethyl-2-methylpropionamide]

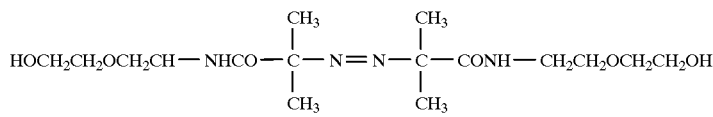

To a constantly stirred mixture comprising 23.0 g of dimethyl 2,2'-azobis(2-methylpropionate) (V-601, a trade name, mfd. by Wako Pure Chemical Industries, Ltd., hereinafter referred to as "V-601"), 23.1 g of 2-(2-aminoethoxy) ethanol and 5 ml of methanol, 9.3 g of a 28 wt. % methanolic solution of sodium methoxide (hereinafter referred to as "28% CH$_3$ONa") was added dropwise. The reaction was carried out with stirring at room temperature for 7 hours. After standing overnight, the reaction mixture was mixed with 50-ml of saturated sodium chloride solution, and extracted with 100 ml of dichloromethane. The organic layer was dried over anhydrous magnesium sulfate and the solvent was distilled off, and there was obtained 28.8 g (yield 76%) of 2,2'-azobis[N-(2-hydroxyethoxy)ethyl-2-methylpropionamide] as a light yellow viscous liquid. 1H-NMR δ ppm (CDCl$_3$): 1.38 (s, 12H, =N—C(CH$_3$)$_2$—), 2.77 (brs, 2H, —OH), 3.57 (m, 12H, —NH—CH$_2$CH$_2$OCH$_2$CH$_2$OH), 3.71 (t, 4H, —O—CH$_2$CH$_2$—OH), 7.11 (brs, 2H, —CONH—).

UV (CH$_3$OH): λ$_{max}$=375 nm. E (1%)=0.7569.

The temperature of 10-hour half life: 97° C.

EXAMPLE 2

Synthesis of Macroazo Compound

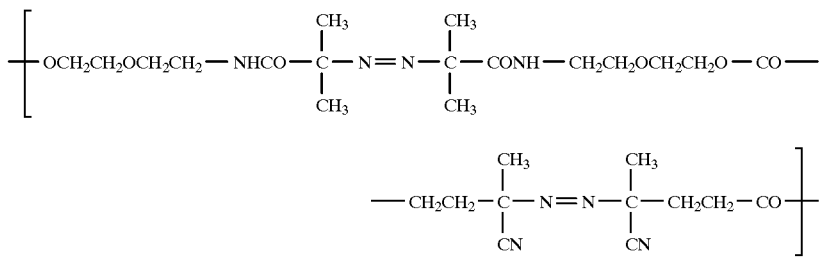

To a constantly stirred mixture comprising 11.2 g of 4,4'-azobis(4-cyanopentanoic acid) (V-501, a trade name, mfd. by Wako Pure Chemical Industries, Ltd., hereinafter referred to as "V-501"), 4.9 g of 4-dimethylaminopyridine (DMAP), 15.1 g of the 2,2'-azobis[N-(2-hydroxyethoxy) ethyl-2-methylpropionamide] obtained in Example 1 and 150 ml of dichloromethane, 18.2 g of dicyclohexylcarbodiimide (DCC) was added. The reaction was carried out with stirring at room temperature for 6 hours. After standing overnight, the resulting crystals were filtered off, and the filtrate was washed with 100 ml of 10% hydrochloric acid solution and 150 ml of saturated sodium chloride solution successively, and dried over anhydrous magnesium sulfate. By distilling off the solvent, there was obtained 20.2 g (yield 81.5%) of the objective compound as a yellow viscous liquid. A GPC measurement revealed that number-average molecular weight of this product was 6,650, and the degree of dispersion thereof was 1.65. Hereinafter, this product is referred to as "MAI-l". $^1$H-NMR δ ppm (CDCl$_3$): 1.34 (s, 12H, =N—C(CH$_3$)$_2$—), 1.67–1.73 (d, 6H, =N—C(CH$_3$)(CN)—), 2.36–2.56 (m, 8H, CO—CH$_2$CH$_2$—), 3.58 (brs, 8H, —NH—CH$_2$CH$_2$OCH$_2$CH$_2$O—), 3.67 (brs, 4H, —NH—CH$_2$CH$_2$O—), 4.24 (brs, 4H, COO—CH$_2$CH$_2$O—), 7.20 (brs, 2H, —CONH—).

UV (CH$_3$OH); $\lambda_{max}$=363 nm. E (1%) =0.6324.

EXAMPLE 3

Production of Styrene-Methyl Methacrylate Block Polymer Using MAI-l (1) First Step, namely Polymerization of Styrene Using MAI-l A mixture of 1.00 g of MAI-l obtained in Example 2, 25.30 g of styrene and 27.00 g of toluene was subjected to a polymerization reaction at 80° C. for 8 hours under a nitrogen stream. After the reaction, the reaction mixture was poured into methanol and precipitated. The deposited polymer was collected by filtration and dried to obtain 18.42 g (yield 70.04%) of the objective azo group-containing polystyrene as a white bulky product. The GPC measurement revealed that this product had a number-average molecular weight of 58,142, a weight-average molecular weight of 184,019, and a degree of dispersion of 3.17. Hereinafter, this product is referred to as PSt*-[1].

(2) Step 2, namely Polymerization of Methyl Methacrylate Using PSt*-[1]

A mixture consisting of 10.01 g of the PSt*-[1] obtained in Paragraph (1), 20.02 g of methyl methacrylate and 100 ml of toluene was subjected to a polymerization reaction under a nitrogen stream at 103° C. for 8 hours. After the reaction, the reaction mixture was poured into methanol and precipitated. The polymer deposited was collected by filtration and dried to obtain 24.17 g (yield 80.49%) of the objective block polymer as a white fibrous product. A GPC measurement revealed that this product had a number-average molecular weight of 61,020, a weight-average molecular weight of 147,251 and a degree of dispersion of 2.41. A $^1$H-NMR measurement using CDCl$_3$ as a solvent for measurement revealed that the copolymer composition of this product was 63.33:36.67 as expressed in terms of styrene:methyl methacrylate ratio by weight.

Experimental Example 1

Solubility Test

The 2,2'-azobis[N-(2-hydroxyethoxy)ethyl-2-methylpropionamide] (hereinafter referred to as "azoamide compound of the present invention") and MAI-1 obtained in Example 2 were taken into a measuring flask. A variety of solvents were added to examine the solubility. The results are shown in Table 1.

TABLE 1

| Solvent | Azoamide compound | MAI-1 |
|---|---|---|
| Water | Soluble | Insoluble |
| Methanol | Soluble | Soluble |
| Acetonitrile | Soluble | Soluble |
| Methylene chloride | Soluble | Soluble |
| Ethyl acetate | Soluble | Soluble |
| Toluene | Insoluble | Insoluble |
| Hexane | Insoluble | Insoluble |

It is apparent from the results shown in Table 1 that the azoamide compound of the present invention obtained in Example 1 is insoluble in toluene and hexane having a low polarity, and soluble in solvents of which polarity is higher than that of toluene and hexane. Further, it is apparent that, the azoamide compound of the present invention is soluble not only in aqueous organic solvents such as methanol and the like but also in non-aqueous organic solvents such as methylene chloride and the like although the azoamide compound of the present invention is a water-soluble compound in itself. In other words, the azoamide compound of the present invention obtained in Example 1 is explicitly excellent in solubility in various solvents.

On the other hand, it is apparent that the macroazo compound of the present invention obtained in Example 2 is insoluble in toluene and hexane having a low polarity, but it is soluble in solvents of which polarity is higher than that of toluene and hexane. It is further known that the macroazo compound of the present invention is soluble not only in aqueous organic solvents such as methanol and the like but also in non-aqueous organic solvents such as methylene chloride and the like, and therefore is excellent in solubility in various solvents.

EXAMPLE 4

Synthesis of 2,2'-azobis[N-(2-hydroxy-ethylamino) ethyl-2-methylpropionamide]

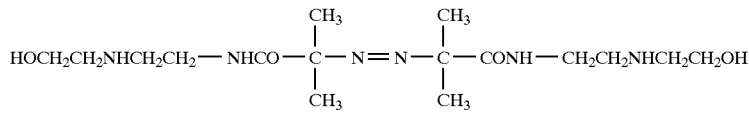

To a constantly stirred mixture comprising 23.0 g of V-601, 22.9 g of 2-(2-aminoethylamino)ethanol and 5 ml of methanol, 4.7 g of 28% $CH_3ONa$ was added dropwise. The reaction was carried out with stirring at room temperature for 8 hours. After standing overnight, the reaction mixture was mixed with 50 ml of saturated sodium chloride solution, and extracted with 100 ml of dichloromethane. The organic layer was dried over anhydrous magnesium sulfate and solvent was distilled off, and there was obtained 29.8 g (yield 80%) of 2,2'-azobis [N-(2-hydroxyethylamino)ethyl-2-methylpropionamide ] of yellow viscous liquid.

$^1$H-NMR δ ppm ($CDCl_3$): 1.39 (s, 12H,=N—C($CH_3$)$_2$—), 2.78 (m, 12H, —CONH—$CH_2CH_2NHCH_2CH_2OH$), 3.46 (m, 4H, —CONH—$CH_2CH_2NH$—), 3.65 (t, 4H, —NH—$CH_2CH_2OH$), 7.14 (brs, 2H, —CONH—).

EXAMPLE 5

Synthesis of Macroazo Compound

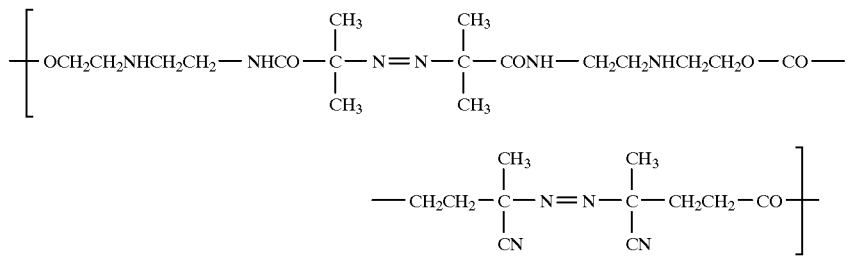

To a constantly stirred mixture comprising 14.0 g of V-501, 6.1 g of DMAP, 18.7 g of 2,2'-azobis[N-(2-hydroxyethylamino)ethyl-2-methylpropionamide ] obtained in Example 4 and 180 ml of dichloromethane, 22.7 g of DCC was added. The reaction was carried out with stirring at room temperature for 8 hours. After standing overnight, deposited crystals were filtered off, and the filtrate was poured into 600 ml of n-hexane to precipitate a macroazo compound. The solvent was removed by decantation, the precipitate was dried under reduced pressure, and there was obtained 28.9 g (yield 93.5%) of the objective compound as a light yellow product. A GPC measurement revealed that the number-average molecular weight of this product was 2,390, and the degree of dispersion thereof was 1.45.

$^1$H-NMR δ ppm ($CDCl_3$): 1.36 (brs, 12H, =N—C($CH_3$)$_2$), 1.72 (brs, 6H, =N—C($CH_3$)(CN)—), 2.46 (brs, 18, —$CH_2CH_2$—COO—$CH_2CH_2$—NH—$CH_2C_2$—), 3.51 (brs, 4H, —NH—$CH_2CH_2NHCO$—), 4.24 (brs, 4H, —COO—$CH_2CH_2$—NH—), 7.44 (brs, 2H, —CONH—).

EXAMPLE 6

A styrene solution containing $4 \times 10^{-4}$ mole/l. of the azoamide compound obtained in Example 1 in an amount of 5 ml was charged in a glass ampoule, and subjected to exhaust of the gas, followed by sealing under reduced pressure. A number of ampoules thus sealed were placed in a constant temperature bath adjusted at 100° C. to initiate the polymerization. After a certain time, an ampoule was taken out of the constant temperature bath and cooled in ice water to terminate the polymerization. Then the polymerization solution in the ampoule was poured into methanol to deposit an polymer, which was filtered and dried at 60° C. for 6 hours under reduced pressure. The obtained polymer was weighed. The conversion was obtained from the styrene amount at the charge and the produced amount of the polymer. The results are shown in Table 2.

EXAMPLE 7

The process of Example 6 was repeated except for using the azoamide compound obtained in Example 4 in place of the azoamide compound obtained in Example 1. The conversion was obtained from the styrene amount at the charge and the produced amount of the polymer. The results are shown in Table 2.

TABLE 2

| Example No. | Polymerization time (hours) | | | | | |
|---|---|---|---|---|---|---|
| | 1 | 2 | 3 | 4 | 5 | 6 |
| 6 | 10.8 | 28.1 | 39.7 | 53.5 | 62.6 | 75.4 |
| 7 | 5.5 | 18.5 | 32.3 | 40.6 | 48.9 | 58.1 |

As is clear from Table 2, the azoamide compounds of the present invention obtained in Examples 1 and 4 have high polymerization activity in the polymerization of styrene.

As has been mentioned above, the present invention provides a novel azoamide compound excellent in solubility in various solvents. The polymer obtained by using said azoamide compound as a polymerization initiator has a hydroxyl group (or amino group) derived from the azoamide compound on the polymer molecular terminal thereof, and therefore various functions can be given to the polymer. Thus, the present invention can contribute to the industry greatly. Further, the present invention provides a novel macroazo compound having two kinds of azo groups different from each other in decomposing activity, in one molecule. By carrying out a multi-step polymerization using the macroazo compound of the present invention, a block polymer block-wise constituted of different repeating units can be obtained efficiently. This is an outstanding effect of the present invention.

What is claimed is:

1. A macroazo compound having repeating units represented by the following formula and having a degree of polymerization of at least 2:

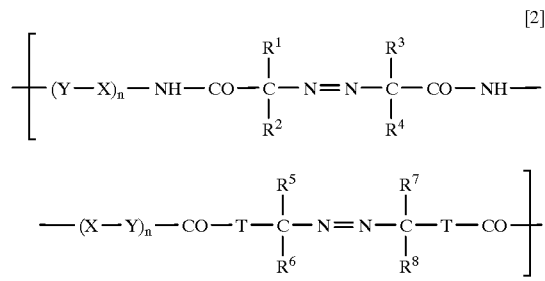

wherein $R^1$ to $R^5$ and $R^7$ are independently an alkyl group; $R^6$ and $R^8$ are independently an alkyl group or a cyano group; X and T are independently an alkylene group; Y is O or NH provided that each Y is the same or different; and n is an integer of 2 or more.

2. A process for producing an a macroazo compound of claim 1, which comprises reacting an azoamide compound represented by the following formula:

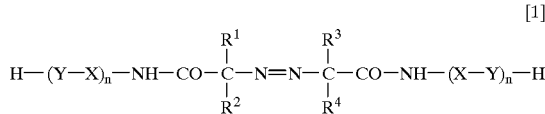

wherein $R^1$ to $R^4$ are independently an alkyl group; X is an alkylene group; Y is O or NH provided that each Y is the same or different; and n is an integer of 2 or more, with an azodicarboxylic acid compound represented by the following formula:

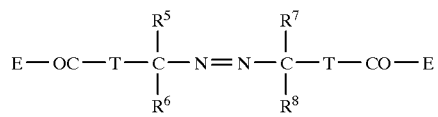

wherein $R^5$ and $R^7$ are independently an alkyl group; $R^6$ and $R^8$ are independently an alkyl group or a cyano group; T is an alkylene group; and E is a hydroxyl group or Z; and Z is a halogen atom.

3. A macroazo initiator comprising a macroazo compound of claim 1.

4. A process for producing a polymer, which comprises polymerizing a monomer in the presence of a macroazo initiator of claim 3.

5. A process according to claim 4, wherein the monomer is a vinyl monomer.

6. A process for producing a block polymer, which comprises, in the first step, polymerizing a monomer in the presence of a macroazo initiator of claim 3 to give an azo group-containing polymer, and then, in the second step, polymerizing a monomer different from that used in the first step in the presence of the azo group-containing polymer.

7. A process according to claim 6, wherein the monomer used in the first step is a vinyl monomer, and that used in the second step is a vinyl monomer different from that used in the first step.

8. A process according to claim 6, wherein the block polymer is styrene-methyl methacrylate block polymer.

9. A macroazo compound according to claim 1, wherein $R^1$ to $R^5$ and $R^7$ are independently an alkyl group having 1 to 6 carbon atoms; $R^6$ and $R^8$ are a cyano group; X and T are independently an alkylene group having 1 to 6 carbon atoms; Y is O or NH provided that each Y is the same or different; and n is an integer of 2 to 4.

10. A macroazo compound according to claim 1, which has repeating units represented by the following formula:

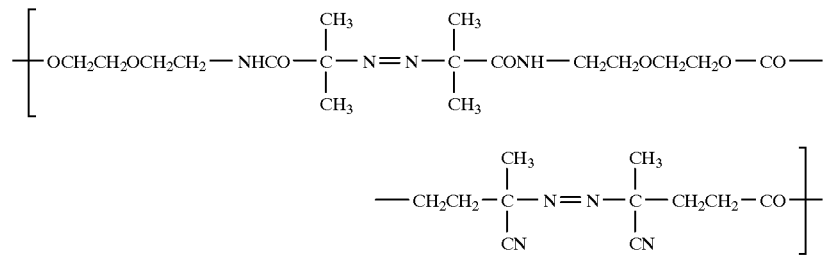

11. A macroazo compound according to claim 1, which has repeating units represented by the following formula:

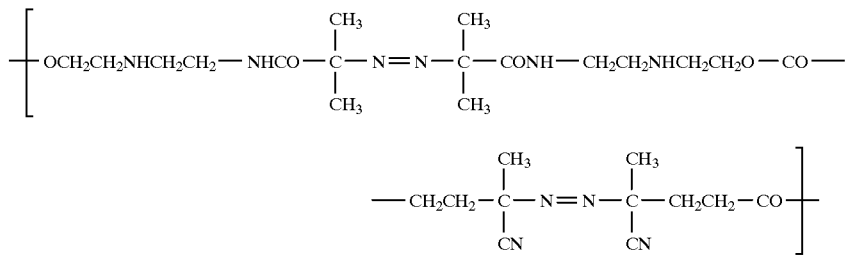

12. A macroazo compound according to claim 1, wherein n is an integer of from 2 to 50.

13. A macroazo compound according to claim 1, where n is an integer of from 2 to 30.

14. A macroazo compound according to claim 1, wherein n is an integer of from 2 to 10.

15. A macroazo compound according to claim 1, wherein n is an integer of from 2 to 4.

16. A macroazo compound according to claim 1, said compound having a degree of polymerization of from 2 to 100.

17. A macroazo compound according to claim 1, said compound having a degree of polymerization of from 2 to 30.

18. A macroazo compound according to claim 1, said compound having a degree of polymerization of from 2 to 100.

* * * * *